United States Patent [19]

Khokhar et al.

[11] Patent Number: 5,011,959

[45] Date of Patent: Apr. 30, 1991

[54] 1,2-DIAMINOCYCLOHEXANE-PLATINUM COMPLEXES WITH ANTITUMOR ACTIVITY

[75] Inventors: Abdul R. Khokhar; Robert A. Newman; Irwin H. Krakoff, all of Houston, Tex.

[73] Assignee: The Board of Regents, The University of Texas System, Austin, Tex.

[21] Appl. No.: 932,176

[22] Filed: Nov. 17, 1986

[51] Int. Cl.$^5$ .................. C07F 15/00; A01N 43/04; A01N 55/02; A61K 31/28
[52] U.S. Cl. .................................. 556/137; 549/206; 514/23; 514/189; 514/492; 127/29; 127/30
[58] Field of Search ................. 556/137; 549/206; 127/29, 30; 514/492, 23, 184

[56] References Cited

U.S. PATENT DOCUMENTS

| | | | |
|---|---|---|---|
| 4,169,846 | 10/1979 | Kidani et al. | 260/429 |
| 4,560,781 | 12/1985 | Totani et al. | 556/137 |
| 4,562,275 | 12/1985 | Speer et al. | 556/7 |
| 4,565,884 | 1/1986 | Andrulis, Jr. et al. | 556/137 |
| 4,575,550 | 3/1986 | Totani | 536/121 |
| 4,577,038 | 3/1986 | Totani et al. | 556/137 |
| 4,578,491 | 3/1986 | Amundsen et al. | 556/137 |
| 4,584,316 | 4/1986 | Rosenberg et al. | 514/492 |
| 4,584,392 | 4/1986 | Smith et al. | 556/137 |
| 4,594,418 | 6/1986 | Speer et al. | 554/225 |
| 4,599,352 | 7/1986 | Narayanan et al. | 514/492 |
| 4,614,811 | 9/1986 | Gandolfi | 556/137 |
| 4,617,189 | 10/1986 | Stockel et al. | 424/162 |
| 4,658,047 | 4/1987 | Vishnurajjala | 556/137 |
| 4,658,048 | 4/1987 | Totani et al. | 556/137 |
| 4,659,849 | 4/1987 | Drobnik et al. | 556/137 |
| 4,661,516 | 4/1987 | Brown, et al. | 514/492 |
| 4,665,210 | 5/1987 | Bitha et al. | 556/137 |
| 4,670,458 | 6/1987 | Hlavka et al. | 514/492 |
| 4,673,754 | 6/1987 | Smith et al. | 556/137 |
| 4,675,336 | 6/1987 | Bitha et al. | 514/492 |
| 4,680,308 | 7/1987 | Schwartz et al. | 514/492 |
| 4,707,352 | 11/1987 | Stavrianpoulos | 424/1.1 |
| 4,720,504 | 1/1988 | Andrulis, Jr. et al. | 514/492 |
| 4,739,087 | 4/1988 | Speer et al. | 556/137 |

FOREIGN PATENT DOCUMENTS

| | | | |
|---|---|---|---|
| 898614 | 5/1984 | Belgium | 556/137 |
| 30039272 | 11/1981 | European Pat. Off. | 556/137 |
| 30098121 | 1/1984 | European Pat. Off. | 556/137 |
| 10113508 | 7/1984 | European Pat. Off. | 556/137 |
| 10130482 | 1/1985 | European Pat. Off. | 556/137 |
| 10136012 | 4/1985 | European Pat. Off. | 556/137 |
| 30155705 | 9/1985 | European Pat. Off. | 556/137 |
| 10185225 | 6/1986 | European Pat. Off. | 556/137 |
| 0193936 | 10/1986 | European Pat. Off. | 556/137 |

OTHER PUBLICATIONS

International Search Report, PCT/U.S. 87/02996, 04/27/88.
Chem. Abstracts, vol. 107(25) #229147d (see therein JP87 59,289 (03/14/87).
Speer et al., "Antitumor Activity of Platinum Complexes of 1,2–Diaminocyclohexane Isomers", J. Clin. Hematology and Onocology, vol. 8, No. 2, 44–50(1978).
Dialog Search Report.
Lexis Search Report, Nov. 17, 1985.
Craciunescu et al., "On the Preparation, Antitumor and Cytotoxic Evaluation of Some New Analogs of the Cis-Dichloro (1,2-Diaminocyclohexane) Platinum(II) Complex", Eur. J. Med. Chem. Clin. Ther., vol. 19, 353–357 (1984).

Primary Examiner—Paul F Shaver
Attorney, Agent, or Firm—Arnold, White & Durkee

[57] ABSTRACT

The present invention comprises a water-soluble square-planar cis-platinum(II) four-coordinate complex having the formula:

trans-R,R-DACH Pt(II) X$_2$ or trans-R,R-DACH Pt(II) Y wherein X is a monovalent cation, two of which are present, selected from the group consisting of cyclopropanecarboxylato, shikimato, saccharatolactone, galacturonato and N,N-dimethyglycinato; wherein Y is a divalent cation selected from the group consisting of citraconato, 1,1-cyclobutanedicarboxylato, 1,1-cyclopropanedicarboxylato, isocitratolactone and Z-iminodiacetato where Z is bound to the nitrogen and is ethyl, propyl, Isopropyl, n-butyl, sec-butyl, ter-butyl, n-amyl, isoamyl or OH.

In one preferred aspect the water-soluble square-planar cis-platinum(II) four-coordinate complex has the formula:

trans-R,R-DACH Pt(II) X$_2$ wherein X is a monovalent cation. Two X substituents are present in the platinum complex. These X substituents are preferably selected from the group consisting of cyclopropanecarboxylato, shikimato, saccharatolactone, galacturonato and N,N-dimethylglycinato. Both X substituents are usually identical butmay be different.

24 Claims, No Drawings

1,2-DIAMINOCYCLOHEXANE-PLATINUM COMPLEXES WITH ANTITUMOR ACTIVITY

BACKGROUND OF THE INVENTION

This invention relates to newly synthesized platinum complexes. The use of these complexes in anti-tumor chemotherapy is also described.

Cis-platinum (CDDP) is a highly effective drug in the treatment of several neoplastic diseases in humans (Loehrer et al. (1984) Ann. Int. Med. V 100, pp 704–713). However, its use is limited by severe systemic toxicity, particularly nephrotoxicity and neurotoxicity (Zwelling et al. Platinum Complexes. In: Pharmacologic principles of cancer treatment (1982) Ed by B. A. Chabner, Saunders, Philadelphia, Penn.). In an attempt to modify the therapeutic index of CDDP, new derivatives have been synthesized during the last decade. However, the development of some promising analogues has been prevented by their low hydrosolubility, which may decrease their potential for clinical use (Burchenal et al. (1979) Cancer Treat. Rep. V 63, pp 1493–1497).

In U.S. Pat. No. 4,256,652 are described certain platinum compounds comprising resolved stereoisomers of 1,2 diaminocyclohexane (DACH). The isomers utilized were cis-DACH, trans-RR-DACH and trans-SS-DACH. The platinum compounds described therein contained, in addition to a resolved DACH isomer, two hydrophilic platinum ligands such as bromide, iodide, nitrate, bromoacetate, sulfate or glucuronate. The platinum compounds comprising the trans-RR-DACH were described as often more therapeutically effective than those bearing cis-DACH.

In European Patent Application number 184107104.6 (public. no. 0130482, Brown et al., published Jan. 1, 1985) many platinum complexes are described. The platinum complexes described therein comprised DACH and carboxylate ligands including:
N-(2-hydroxyethyl)-iminodiacetato
N-(2-acetamido)-diacetato
N-methyliminodiacetato
trans-1,2-cylclopropanedicarboxylato
trans-1,2cyclobutanedicarboxylato
glycinato
isocitratomonoethylester
D,L-isocitratolactone
ascorbato
D-monosaccharato
D-saccharato-1,4-lactone.

These complexes comprised DACH of an undefined stereochemical structure and, in contrast to the complexes of the present invention, was presumably a racemic mixture of all possible DACH stereoisomers. These complexes are further distinguished from those of the present invention by virtue of their carboxylato ligands, analogous in some cases but different.

Featured advantages of the compounds of the present invention include:
(1) High antitumor activity;
(ii) Lowered potential to produce nephrotoxicity;
(iii) Lack of cross-resistance in in vitro antitumor cell cultures resistant to cisplatin (i.e., L1210/cisplatin);
(iv) High aqueous solubility

SUMMARY OF THE INVENTION

The present invention comprises a water-soluble square-planar cis-platinum(II) four-coordinate complex having the formula:

trans-R,R-DACH Pt(II) $X_2$ or trans-R,R-DACH Pt(II) Y wherein X is a monovalent cation, two of which are present, selected from the group consisting of cyclopropanecarboxylato, shikimato, saccharatolactone, galacturonato and N,N-dimethylglycinato; wherein Y is a divalent cation selected from the group consisting of citraconato, 1,1-cyclobutanedicarboxylato, 1,1-cyclopropanedicarboxylato, isocitratolactone and Z-iminodiacetato where Z is bound to the nitrogen and is ethyl, propyl, isopropyl, n-butyl, sec-butyl, ter-butyl, n-amyl, isoamyl or OH.

In one preferred aspect the water-soluble square-planar cis-platinum(II) four-coordinate complex has the formula:

trans-R,R-DACH Pt(II) $X_2$ wherein X is a monovalent cation. Two X substituents are present in the platinum complex. These X substituents are preferably selected from the group consisting of cyclopropanecarboxylato, shikimato, saccharatolactone, galacturonato and N,N-dimethylglycinato. Both X substituents are usually identical but may be different.

When the water-soluble square-planar cis-platinum(II) four-coordinate complex has the formula:

trans-R,R-DACH Pt(II) Y the Y substituent is preferably a single divalent cation selected from the group consisting of citraconato, 1,1-cyclobutanedicarboxylato, 1,1-cyclopropanedicarboxylato, isocitratolactone and Z-iminodiacetato where Z is bound to the nitrogen and is ethyl, propyl, isopropyl, n-butyl, sec-butyl, ter-butyl, n-amyl, isoamyl or OH.

In a most preferred embodiment the water-soluble square-planar cis-platinum(II) four-coordinate complex having the formula:

trans-R,R-DACH Pt(II) Y wherein Y is Z-iminodiacetato where Z is ethyl, propyl, isopropyl, n-butyl, sec-butyl, ter-butyl, n-amyl, isoamyl or OH.

In an important aspect the complexes of the present invention demonstrate marked utility in a process for treating animals having tumors sensitive to these complexes. This process comprises administering to said animals a pharmaceutical composition consisting essentially of an therapeutically anti-tumor effective amount of the water-soluble square-planar cis-platinum(II) four-coordinate complex described above. For this process a pharmaceutical composition comprising a platinum complex of the present invention may be utilized. This pharmaceutical composition is preferably in a unit dosage form suitable for administration to an animal afflicted with tumor cells. The unit dosage comprises a therapeutically anti-tumor effective amount of the water-soluble square-planar cis-platinum(II) four-coordinate complex. The therapeutically anti-tumor effective amount should usually be between 1 mg/kg and 20 mg/kg but may vary considerably based upon tumor type and the judgement of the attending therapist. Likewise the dosage frequency and duration are variable.

DESCRIPTION OF THE PREFERRED EMBODIMENT

Cisplatin is an important anticancer drug which has the potential to produce life-threatening nephrotoxicity. While new platinum antitumor drugs have been produced which are relatively free from the potential to produce renal injury, many experience significant water solubility problems. The present invention comprises several diaminocyclohexane platinum (DACH-Pt) antitumor complexes which: (1) retain or surpass the antitumor efficacy of cisplatin, (2) are non-cross resistant with cisplatin in a murine leukemia cell line which is specifically resistant to this drug (L1210/cisplatin), (3) are non-nephrotoxic and (4) are water soluble. These compounds offer distinct advantages as antitumor agents over the use of cisplatin. Table 1 lists the complexes of the present invention.

TABLE 1

COMPOUNDS OF THE PRESENT INVENTION

| Number | Compound |
|---|---|
| 1 | N-ethyliminodiacetato(trans-R,R-DACH)Pt(II) $H_2O$ |
| 2 | N-propyliminodiacetato(trans-R,R-DACH)Pt(II) $2H_2O$ |
| 3 | N-butyliminodiacetato(trans-R,R-DACH)Pt(II) $2H_2O$ |
| 4 | N-amyliminodiacetato(trans-R,R-DACH)Pt(II) $H_2O$ |
| 5 | N-isopropyliminodiacetato(trans-R,R-DACH)Pt(II) $2H_2O$ |
| 6 | N-isoamyliminodiacetato(trans-R,R-DACH)Pt(II) |
| 7 | N-sec-butyliminodiacetato(trans-R,R-DACH)Pt(II) $2H_2O$ |
| 8 | N-ter-butyliminodiacetato(trans-R,R-DACH)Pt(II) $3H_2O$ |
| 9 | N-hydroxyliminodiacetato(trans-R,R-DACH)Pt(II) $2H_2O$ |
| 10 | Citraconato(trans-R,R-DACH)Pt(II) $1H_2O$ |
| 11 | 1,1-Cyclobutanedicarboxylato(trans-R,R-DACH)Pt(II) $1\frac{1}{2} H_2O$ |
| 12 | 1,1-Cyclobutanedicarboxylato(trans-S,S-DACH)Pt(II) $2H_2O$ |
| 13 | 1,1-Cyclobutanedicarboxylato(cis-DACH)Pt(II) $1\frac{1}{2} H_2O$ |
| 14 | 1,1-Cyclopropanedicarboxylato(trans-R,R-DACH)Pt(II) $H_2O$ |
| 15 | Isocitratolactone(trans-R,R-DACH)Pt(II) $H_2O$ |
| 16 | Cis-bis-cyclopropanecarboxylato(trans-R,R-DACH)Pt(II) $H_2O$ |
| 17 | Cis-bis-shikimato(trans-R,R-DACH)Pt(II) $H_2O$ |
| 18 | Cis-bis-saccharatolactone(trans-R,R-DACH)Pt(II) $H_2O$ |
| 19 | Cis-bis-galacturonato(trans-R,R-DACH)Pt(II) $2H_2O$ |
| 20 | Cis-bis-N,N-dimethylglycinato(trans-R,R-DACH)Pt(II) $2H_2O$ |

DACH = 1,2-diaminocyclohexane

These examples are presented to described preferred embodiments and utilities of the present invention and are not meant to limit the present invention unless otherwise stated in the claims appended hereto.

EXAMPLE 1

Cis-bis-dichloro(trans-R,R-DACH)platinum(II)

To an aqueous filtered solution of 16.6 g $K_2PtCl_4$ (0.04 mole in 250 ml of water) 4.56 g (8.4 mmole) of trans-R,R-DACH was added. The reaction mixture was stirred at room temperature for 6-8 hours. A yellow solid was precipitated, filtered, washed with water, methanol and finally with acetone. The final product was dried under vacuum.

Yield = 56%

Cis-bis-dichloro(trans-S,S-DACH)platinum(II) and cis-bis-dichloro(cis-DACH)platinum(II) were prepared in an analogous manner using stoichiometric amounts (ca. 1 mmole) of $K_2PtCl_4$ and the respective DACH isomers, i.e. trans-S,S and cis-.

EXAMPLE 2

Sulfato (DACH)platinum(II) $H_2O$

Dichloro (DACH)platinum(II), [DACH being trans-R,R-, trans-S,S- or cis isomer], (1.0 g; 2.6 mmole) was suspended ion water (20 ml), and a solution of $Ag_2SO_4$ (0.75 g; 2.4 mmole) in water (150 ml) was added. The reaction mixture was stirred at room temperature for 24 hours in the dark. The precipitated AgCl was filtered off, and the yellow filtrate was evaporated to dryness at 45°-50° C. under reduced pressure using a rotary evaporator. A yellow product was obtained and dried over $P_2O_5$ under vacuum.

Yield: 90%

EXAMPLE 3

N-ethyliminodiacetato(trans-R,R-DACH)platinum (II) $H_2O$

Sulfato (trans-R,R-DACH)platinum(II) $H_2O$ (0.423 g) was dissolved in water (25 ml) and an aqueous solution of barium ethyliminodiacetate (0.332 g) was added thereto. The reaction mixture was stirred for 30 minutes at room temperature. $BaSO_4$ precipitate was filtered and filtrate was evaporated to dryness at 40°-45° C. under reduced pressure using a rotary evaporator. A cream-colored solid was obtained which was finally purified from n-propanol. The product was dried over $P_2O_5$ in vacuo.

Yield: 56%

The analytical data for the product are set forth in Table 2. Other complexes of the invention, i.e., N-propyliminodiacetato, N-butyliminodiacetato,- Namyliminodiacetato, N-isopropyliminodiacetato, N-isoamyliminodiacetato, N-sec-butyliminodiacetato, N-ter butyliminodiacetato and N-hydroxyliminodiacetato were prepared in an analogous manner to the above-mentioned method using stoichiometric amounts (cal mmole) sulfato (trans-R,R-DACH)-platinum(II) $H_2O$ and the respective barium salts of N-substituted iminodiacetic acids.

EXAMPLE 4

Citraconato(trans-R,R-DACH)Pt(II) $2H_2O$

Sulfato(trans-R,R-DACH)platinum(II) $H_2O$ (0.423 g) was dissolved in water (20 ml) and solution of barium citraconate prepared in situ (citraconic acid (0.13 g) and $Ba(OH)_2$ $8H_2O$ (0.3 g) in $H_2O$) was added thereto. The reaction mixture was stirred for 30 minutes at room temperature. Barium sulfate precipitate was filtered and the filtrate was evaporated to dryness at 40°-45° C. under reduced pressure using a rotary evaporator. A cream colored product was obtained which was further dried over $P_2O_5$ in vacuo.

The analytical data for these complexes are set forth in Table 2.

EXAMPLE 5

1,1-Cyclobutanedicarboxylato (trans-R,R-DACH)platinum(II)

Sulfato(trans-R,R-DACH)platinum(II) $H_2O$ (0.423 g) was dissolved in water (100 ml) and barium 1,1-cyclobutanedicarboxylate prepared in situ [1,1-cyclobutanedicarboxylic acid (0.13 g) and $Ba(OH)_2$ 8H$_2$O (0.3 g) in water (200 ml)] was added thereto. The reaction mixture was stirred for 30 minutes at room temperature. Barium sulfate was filtered and the filtrate was evaporated to dryness at 40°–45° C. under reduced pressure using a rotary evaporator. Solid was obtained which was purified from water. The final product was dried in vacuo.

1,1-Cyclobutanedicarboxylato(trans-S,S-DACH)-platinum(II) and 1,1-cyclobutanedicarboxylato(cis-DACH) platinum(II) were prepared in an analogous manner to the above mentioned method but using trans-S,S-DACH and cis-DACH ligands.

The analytical data for the products are set forth in Table 2.

EXAMPLE 6

Cis-bis-cyclopropanecarboxylato (trans-R,R-DACH)platinum(II)

Sulfato(trans-R,R-DACH)platinum(II). H$_2$O (0.423 g) was dissolved in water (20 ml) and an aqueous solution of barium cyclopropanecarboxylate prepared in situ. The reaction mixture was added thereto. The barium cyclopropanecarboxylic acid was prepared by mising 0.172 g cyclopropanecarboxylic acid and 0.3 g Ba(OH)$_2$. 8H$_2$O in water, stirred for 30 minutes at room temperature. Barium sulfate was removed by filtration and filtrate was evaporated to dryness at 40°–45° C. under reduced pressure using a rotary evaporator. A cream colored solid was obtained which was purified from methanol. The final product was dried over P$_2$O$_5$ in vacuo.

1,1-Cyclopropanedicarboxylato(trans-R,R-DACH)-platinum(II) was prepared in an analogous manner to this method using stoichiometric amounts of Ba-1,1-cyclopropanedicarboxylate ligand.

The analytical data for the products are set forth in Table 2.

EXAMPLE 7

Cis-bis-shikimato(trans-R,R-DACH)platinum(II)

Sulfato(trans-R,R-DACH)platinum(II) H$_2$O (0.423 g) was dissolved in water (20 ml) and a solution of barium shikimate (0.483 g in 50 ml water) was added thereto. The reaction mixture was stirred for 30 minutes at room temperature. Barium sulfate precipitate was filtered off and the filtrate was evaporated to dryness at 40°–45° C. under vacuum using a rotary evaporator. A cream colored solid was obtained which was purified from water. The final product was dried over P$_2$O$_5$ in vacuo.

Cis-bis-galacturonato (trans-R,R-DACH)platinum(II) cis-bis-saccharatolactone(trans-R,RR-DACH)-platinum(II), isocitratolactone (trans-R,R-DACH)-platinum(II) and cis-bis-N,N-dimethyl-glycinato(trans-R,R-DACH)platinum(II) were prepared in an analogous manner to this method using stoichiometric amounts of barium salts of respective acids.

The analytical data for the products are set forth in Table 2.

TABLE 2

| Compound No. | ANALYTICAL DATA | | | | | |
|---|---|---|---|---|---|---|
| | % Observed | | | % Calculated | | |
| | C | H | N | C | H | N |
| 1 | 29.99 | 5.44 | 8.02 | 29.63 | 5.21 | 8.64 |
| 2 | 29.85 | 5.12 | 7.61 | 30.11 | 5.64 | 8.10 |
| 3 | 31.52 | 5.72 | 7.55 | 31.58 | 5.87 | 7.89 |
| 4 | 33.17 | 5.71 | 7.47 | 32.96 | 6.08 | 7.69 |
| 5 | 30.08 | 5.46 | 7.65 | 30.11 | 5.64 | 8.10 |

TABLE 2-continued

| Compound No. | ANALYTICAL DATA | | | | | |
|---|---|---|---|---|---|---|
| | % Observed | | | % Calculated | | |
| | C | H | N | C | H | N |
| 6 | 32.85 | 5.62 | 6.42 | 32.96 | 6.08 | 7.64 |
| 7 | 31.31 | 5.49 | 7.42 | 31.58 | 5.87 | 7.63 |
| 8 | 31.09 | 5.81 | 7.25 | 30.54 | 6.04 | 7.63 |
| 9 | 23.77 | 4.38 | 7.76 | 23.53 | 4.94 | 8.23 |
| 10 | 28.95 | 4.55 | 6.21 | 29.0 | 4.39 | 6.15 |
| 11 | 29.83 | 4.80 | 5.74 | 30.1 | 4.81 | 5.85 |
| 12 | 29.44 | 4.49 | 5.19 | 29.56 | 4.92 | 5.74 |
| 13 | 30.13 | 4.32 | 5.55 | 30.13 | 4.81 | 5.55 |
| 14 | 28.98 | 4.51 | 6.03 | 29.00 | 4.61 | 6.15 |
| 15 | 28.30 | 3.98 | 5.25 | 28.85 | 4.00 | 5.61 |
| 16 | 33.30 | 5.30 | 5.66 | 33.79 | 5.23 | 5.63 |
| 17 | 36.03 | 5.33 | 4.00 | 35.66 | 5.05 | 4.16 |
| 18 | 29.32 | 4.43 | 3.69 | 29.00 | 4.15 | 3.75 |
| 19 | 29.34 | 5.07 | 3.66 | 29.53 | 4.65 | 3.83 |
| 20 | 30.96 | 6.26 | 10.15 | 30.60 | 6.20 | 10.20 |

EXAMPLE 8

The in vitro antitumor activities of the complexes of the invention

Wild-type L1210 leukemic cells were grown as a suspension culture in McCoy's 5A medium supplemented with 10% horse serum, glutamine, streptomycin and penicillin at 37° C., 95% relative humidity and 5% CO$_2$. Four ml of cell suspension (10$^5$ cells/ml) were added to culture tubes and the appropriate amount of drug was added (to yield 0.01, 0.1, 1 or 10 ug/ml final concentration) to the culture tubes. After 72 hours of incubation, the cell concentration in control and experimental cultures were determined with the aid of the Coulter counter model ZB$_f$ and the percent of growth inhibition calculated. The in vitro cytotoxicities of platinum complexes of the present invention are shown in Table 3.

TABLE 3

| IN VITRO CYTOTOXICITY | |
|---|---|
| Compound No. | ID$_{50}$ (ug/ml) |
| 1 | 0.73 |
| 2 | 0.75 |
| 3 | 0.74 |
| 4 | 3.00 |
| 5 | 0.85 |
| 6 | N.D. |
| 7 | 0.65 |
| 8 | N.D. |
| 9 | 0.76 |
| 10 | 5.00 |
| 11 | N.D. |
| 12 | 1.65 |
| 13 | 3.30 |
| 14 | 0.66 |
| 15 | 0.67 |
| 16 | 0.55 |
| 17 | 3.20 |
| 18 | 1.40 |
| 19 | 0.90 |
| 20 | 3.5 |

EXAMPLE 9

In vivo antitumor activities of the complexes of the invention

BDF$_1$ mice were inoculated intraperitoneally with 10$^6$ L1210 cells. About 24 hours after inoculation (day 1), the mice were injected intraperitoneally with varying doses of complexes of the present invention. Six mice were used for each dosage level with an equal number of mice inoculated with $10^6$ L1210 cells being left untreated as controls. The results [% T/C=(survival time of treated animals/survival time of control animals)×100] are set forth below. Long-term survival signify that animals were alive 30 days after tumor inoculation. These results are set forth in Table 4.

TABLE 4
IN VIVO ANTITUMOR ACTIVITIES

| Compound No. | Optimal Dose (mg/kg) | Days of Administration | % T/C | Long-term Survivors |
|---|---|---|---|---|
| 1 | 50 | 1 | 125 | — |
|   | 12.5 | 1,5,9 | 324 | 1/6 |
|   | 3.15 | 1–9 | 434 | 4/6 |
| 2 | 56 | 1 | 129 | — |
| 3 | 12.5 | 1 | 147 | — |
|   | 12.5 | 1,5,9 | 318 | 2/6 |
| 4 | 50 | 1 | 158 | — |
|   | 25 | 1,5,9 | 227 | 2/6 |
| 5 | 50 | 1 | 155 | — |
|   | 12.5 | 1,5,9 | 324 | 1/6 |
| 6 | 50 | 1 | 145 | — |
|   | 12.5 | 1,5,9 | 150 | — |
| 7 | 6.25 | 1,5,9 | 282 | 2/6 |
| 8 | 6.25 | 1,5,9 | 271 | 1/6 |

TABLE 4-continued
IN VIVO ANTITUMOR ACTIVITIES

| Compound No. | Optimal Dose (mg/kg) | Days of Administration | % T/C | Long-term Survivors |
|---|---|---|---|---|
| 9 | 50 | 1 | 156 | — |
|   | 25 | 1,5,9 | 265 | — |
| 10 | 25 | 1,5,9 | 200 | — |
| 11 | 50 | 1 | 147 | — |
|    | 12.5 | 1,5,9 | 140 | — |
|    | 6.25 | 1–9 | 398 | 3/6 |
| 12 | 12.5 | 1–9 | 120 | — |
| 13 | 12.5 | 1–9 | 253 | 1/6 |
| 15 | 6.25 | 1,5,9 | 253 | — |
| 16 | 12.5 | 1,5,9 | 283 | — |
| 17 | 25 | 1,5,9 | 184 | — |
| 19 | 12.5 | 1,5,9 | 238 | — |

EXAMPLE 10

Structural Formulas

Structural formulas for compounds of the present invention described in Tables 1 and 2 and elsewhere herein are shown in Table 5 (not including water of hydration, which are not critical).

TABLE 5
STRUCTURAL FORMULAS OF THE WATER-SOLUBLE SQUARE-PLANAR CIS-PLATINUM FOUR-COORDINATE COMPLEXES OF THE PRESENT INVENTION

| COMPOUND NUMBER | NAME | STRUCTURE |
|---|---|---|
| 1. | N-ethyliminodiacetato(trans-R,R-DACH)Pt(II)H$_2$O: | (structure: cyclohexane-diamine coordinated to Pt with N-ethyliminodiacetato ligand: Pt bonded to two OOC—CH$_2$ groups joining to N—C$_2$H$_5$) | also described as trans-R,R-DACH Pt(II)Y, where Y is the divalent cation Z-iminoiacetato and Z is ethyl bound to the nitrogen.

| 2. | N-propyliminodiacetato(trans-R,R-DACH)Pt(II)2H$_2$O | (structure: DACH-Pt with N—CH$_2$—CH$_2$—CH$_3$ iminodiacetato) | also described as trans-R,R-DACH Pt(II)Y where Y is the divalent cation Z-iminodiacetato and Z is propyl bound to the nitrogen.

| 3. | N-butyliminodiacetato(trans-R,R-DACH)Pt(II)2H$_2$O | (structure: DACH-Pt with N—CH$_2$CH$_2$CH$_2$CH$_3$ iminodiacetato) | also described as compounds 1 and 2 but with Z being butyl.

| 4. | N-amyliminodiacetato(trans-R,R-DACH)Pt(II)2H$_2$O | (structure: DACH-Pt with N—(CH$_2$)$_4$CH$_3$ iminodiacetato) | also described as compound 1–3 but with Z being amyl.

TABLE 5-continued
STRUCTURAL FORMULAS OF THE WATER-SOLUBLE SQUARE-PLANAR CIS-PLATINUM FOUR-COORDINATE COMPLEXES OF THE PRESENT INVENTION

| COMPOUND NUMBER | NAME | STRUCTURE |
|---|---|---|
| 5. | N-isopropyliminodiacetato(trans-R,R-DACH) Pt(II)2H$_2$O | 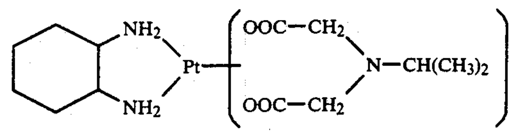 |
| | also described as compounds 1-4 but with Z being isopropyl. | |
| 6. | N-isoamyiminodiacetato(trans-R,R-DACH) Pt(II) | 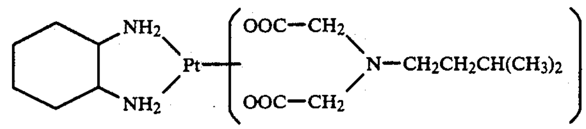 |
| | also described as compounds 1-5 but with Z being isoamyl. | |
| 7. | N-sec-butyliminodiacetato(trans-R,R-DACH) Pt(II)2H$_2$O | 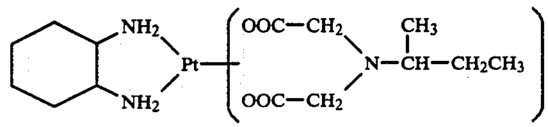 |
| | also described as compounds 1-6 but with Z being sec butyl. | |
| 8. | N-t-butyliminodiacetato(trans-R,R-DACH) Pt(II)3H$_2$O | 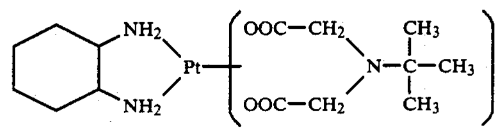 |
| | also described as compounds 1-7 but with Z being tertiary butyl. | |
| 9. | N-hydroxyiminodiacetato(trans-R,R-DACH) Pt(II)2H$_2$O | 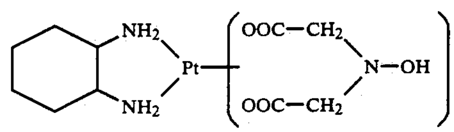 |
| | also described as compounds 1-8 but with Z being hydroxy. | |
| 10. | Citraconato(trans-R,R-DACH) Pt(II)H$_2$O | 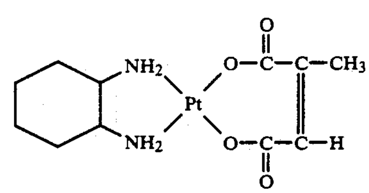 |
| | also described as trans-R,R-DACH Pt(II)Y where Y is the divalent cation citraconato. | |
| 11. | 1,1-cyclobutanedicarboxylato(trans-R,R-DACH) Pt(II)1½H$_2$O | 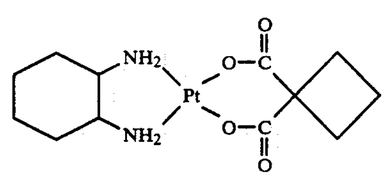 |
| | also described as compound 10 but with Y being the divalent cation 1,1 cyclobutanedicarboxylato. | |
| 12. | Same as compound 11 but with 2H$_2$O. | |

TABLE 5-continued
STRUCTURAL FORMULAS OF THE WATER-SOLUBLE SQUARE-PLANAR CIS-PLATINUM FOUR-COORDINATE COMPLEXES OF THE PRESENT INVENTION

| COMPOUND NUMBER | NAME | STRUCTURE |
|---|---|---|
| 13. | Same as compound 11 but with (cis-DACH) in place of (trans-R,R-DACH). | |
| 14. | 1,1-cyclopropanedicarboxylato(trans-R,R-DACH) Pt(II)H$_2$O<br><br>also described as compound 10 but with Y being the divalent cation 1,1-cyclopropanedicarboxylato. | 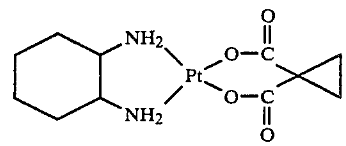 |
| 15. | Isocitratolactone(trans-R,R-DACH) Pt(II)H$_2$O<br><br>also described as compound 10 but with Y being the divalent cation isocitratolactone. | 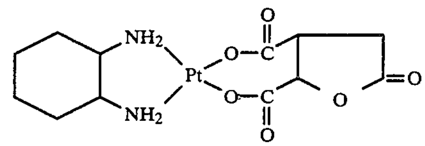 |
| 16. | Cis-bis-cyclopropanecarboxylato(trans-R,R-DACH) Pt(II)H$_2$O<br><br>also described as trans-R,R-DACH Pt(II)X$_2$ where X is the monovalent cation cyclopropanecarboxylato. | 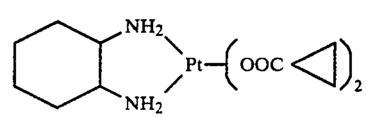 |
| 17. | Cis-bis-shikimato(trans-R,R-DACH) Pt(II)H$_2$O<br><br>also described as compound 16 but with X being the monovalent cation shikimato. | 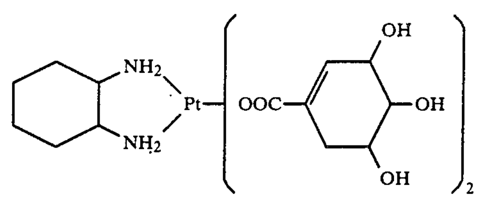 |
| 18. | Cis-bis-saccharatolactone(trans-R,R-DACH) Pt(II)H$_2$O<br><br>also described as compound 16 but with X being the monovalent cation saccharatolactone. | 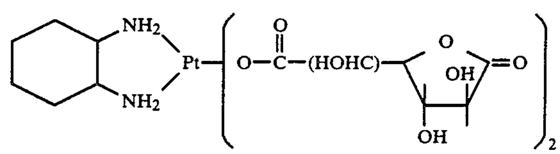 |
| 19. | Cis-bis-galacturonato(trans-R,R-DACH) Pt(II)2H$_2$O<br><br>also described as compound 16 but with Z being the monovalent cation galacturonato. | 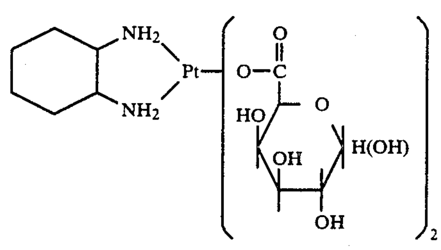 |

TABLE 5-continued
STRUCTURAL FORMULAS OF THE WATER-SOLUBLE SQUARE-
PLANAR CIS-PLATINUM FOUR-COORDINATE COMPLEXES
OF THE PRESENT INVENTION

| COMPOUND NUMBER | NAME | STRUCTURE |
|---|---|---|
| 20. | Cis-bis-N—N-Dimethylglycinato(trans-R,R-DACH) Pt(II)2H$_2$O | | also described as compound 16 but with X being the monovalent cation N,N-dimethylglycinato.

Changes may be made in the elements and reagents or in the steps or the sequence of steps of the methods described herein without departing from the content and scope of the invention as defined in the following claims.

What is claimed is:

1. A water-soluble square-planar cis-platinum(II) four-coordinate complex having the formula:

trans-R,R-DACH Pt(II) X$_2$ or trans-R,R-DACH Pt(II) Y wherein X is a monovalent cation, selected from the group consisting of galacturonato and N,N-dimethylglycinato; wherein Y is a divalent cation selected from the group consisting of citraconato, 1,1-cyclobutanedicarboxylato, 1,1-cyclopropanedicarboxylato, and Z-iminodiacetato where Z is bound to nitrogen and is ethyl, propyl, isopropyl, n-butyl, sec-butyl, ter-butyl, n-amyl, isoamyl or OH.

2. A water-soluble square-planar cis-platinum(II) four-coordinate complex having the formula:

trans-R,R-DACH Pt(II) X$_2$ wherein X is a monovalent cation, selected from the group consisting of galacturonato and N,N-dimethylglycinato.

3. A water-soluble square-planar cis-platinum(II) four-coordinate complex having the formula:

trans-R,R-DACH Pt(II) Y wherein Y is a divalent cation selected from the group consisting of citraconato, 1,1-cyclobutanedicarboxylato, and Z-iminodiacetato where Z is bound to nitrogen and is ethyl, propyl, isopropyl, n-butyl, sec-butyl, ter-butyl, n-amyl, isoamyl or OH.

4. A water-soluble square-planar cis-platinum(II) four-coordinate complex having the formula:

trans-R,R-DACH Pt(II) Y wherein Y is Z-iminodiacetato where Z is bound to the nitrogen and is ethyl, propyl, isopropyl, n-butyl, sec-butyl, ter-butyl, n-amyl, isoamyl or OH.

5. A pharmaceutical composition in unit dosage form suitable for administration to an animal having a tumor sensitive to a platinum complex of claim 1, the composition comprising a therapeutically anti-tumor effective amount of a water-soluble square-planar cis-platinum(II) four-coordinate complex having the formula:

trans-R,R-DACH Pt(II) X$_2$ or trans-R,R-DACH Pt(II) Y wherein X is a monovalent cation, selected from the group consisting of galacturonato and N,N-dimethylglycinato; where Y is a divalent cation selected from the group consisting of citraconato, 1,1-cyclopropanedicarboxylato, and Z-iminodiacetato where Z is bound to nitrogen and is ethyl, propyl, isopropyl, n-butyl, sec-butyl, ter-butyl, n-amyl, isoamyl or OH and a pharmaceutically acceptable carrier therefor.

6. A pharmaceutical composition in unit dosage form suitable for administration to an animal having a tumor sensitive to a platinum complex of claim 2, the composition comprising a therapeutically anti-tumor effective amount of a water-soluble square-planar cis-platinum(II) four-coordinate complex having the formula:

trans-R,R-DACH Pt(II) X$_2$ wherein X is a monovalent cation, two of which are present, selected from the group consisting of galacturonato and N,N-dimethylglycinato and a pharmaceutically acceptable carrier therefor.

7. A pharmaceutical composition in unit dosage form suitable for administration to an animal having a tumor sensitive to a platinum complex of claim 3, the composition comprising a therapeutically anti-tumor effective amount of a water-soluble square-planar cis-platinum(II) four-coordinate complex having the formula:

trans-R,R-DACH Pt(II) Y wherein Y is a divalent cation selected from the group consisting of citraconato, 1,1-cyclobutanedicarboxylato, and Z-iminodiacetato where Z is bound to nitrogen and is ethyl, propyl, isopropyl, n-butyl, sec-butyl, ter-butyl, n-amyl, isoamyl or OH and a pharmaceutically acceptable carrier therefor.

8. A pharmaceutical composition in unit dosage form suitable for administration to an animal having a tumor sensitive to a platinum complex of claim 4, the composition comprising a therapeutically anti-tumor effective amount of a water-soluble square-planar cis-platinum(II) four-coordinate complex having the formula:

trans-R,R-DACH Pt(II) Y wherein Y is Z-iminodiacetato where Z is bound to the nitrogen and is ethyl, propyl, isopropyl, n-butyl, sec-butyl, ter-butyl, n-amyl, isoamyl or OH and a pharmaceutically acceptable carrier therefor.

9. A water-soluble square-planar cis-platinum(II) four-coordinate complex having the formula:

trans-R,R-DACH Pt(II) $X_2$ wherein X is N,N-dimethylglycinato.

10. A water-soluble square-planar cis-platinum(II) four-coordinate complex having the formula:

trans-R,R-DACH Pt(II) $X_2$ wherein X is galacturonato.

11. A water-soluble square-planar cis-platinum(II) four-coordinate complex having the formula:

trans-R,R-DACH Pt(II) Y wherein Y is citraconato.

12. A water-soluble square-planar cis-platinum(II) four-coordinate complex having the formula:

trans-R,R-DACH Pt(II) Y wherein Y is 1,1-cyclobutanedicarboxylato.

13. A water-soluble square-planar cis-platinum(II) four-coordinate complex having the formula:

trans-R,R-DACH Pt(II) Y wherein Y is isocitratolactone.

14. A water-soluble square-planar cis-platinum(II) four-coordinate complex having the formula:

trans-R,R-DACH Pt(II) Y wherein Y is Z-iminodiacetato where Z is bound to nitrogen and is ethyl.

15. A water-soluble square-planar cis-platinum(II) four-coordinate complex having the formula:

trans-R,R-DACH Pt(II) Y wherein Y is Z-iminodiacetato where Z is bound to nitrogen and is propyl.

16. A water-soluble square-planar cis-platinum(II) four-coordinate complex having the formula:

trans-R,R-DACH Pt(II) Y wherein Y is Z-iminodiacetato where Z is bound to nitrogen and is isopropyl.

17. A water-soluble square-planar cis-platinum(II) four-coordinate complex having the formula:

trans-R,R-DACH Pt(II) Y wherein Y is Z-iminodiacetato where Z is bound to nitrogen and is n-butyl.

18. A water-soluble square-planar cis-platinum(II) four-coordinate complex having the formula:

trans-R,R-DACH Pt(II) Y wherein Y is Z-iminodiacetato where Z is bound to nitrogen and is sec-butyl.

19. A water-soluble square-planar cis-platinum(II) four-coordinate complex having the formula:

trans-R,R-DACH Pt(II) Y wherein Y is Z-iminodiacetato where Z is bound to nitrogen and is ter-butyl.

20. A water-soluble square-planar cis-platinum(II) four-coordinate complex having the formula:

trans-R,R-DACH Pt(II) Y wherein Y is Z-iminodiacetato where Z is bound to nitrogen and is n-amyl.

21. A water-soluble square-planar cis-platinum(II) four-coordinate complex having the formula:

trans-R,R-DACH Pt(II) Y wherein Y is Z-iminodiacetato where Z is bound to nitrogen and is isoamyl.

22. A water-soluble square-planar cis-platinum(II) four-coordinate complex having the formula:

trans-R,R-DACH Pt(II) Y wherein Y is Z-iminodiacetato where Z is bound to nitrogen and is OH.

23. A water soluble square-planar cis-platinum(II) four-coordinate complex having the formula:

cis-DACH Pt(II) Y wherein Y is 1,1-cyclobutanedicarboxylato.

24. A water soluble square-planar cis-platinum(II) four-coordinate complex having the formula:

trans-S,S-DACH Pt(II) Y wherein Y is 1,1-cyclobutanedicarboxylato.

* * * * *

UNITED STATES PATENT AND TRADEMARK OFFICE
CERTIFICATE OF CORRECTION

PATENT NO.    : 5,011,959
DATED         : June 27, 1991
INVENTOR(S)   : Abdul R. Khokhar, Robert A. Newman and Irwin H. Krakoff It is certified that error appears in the above-identified patent and that said Letters Patent is hereby corrected as shown below:

Title page,
Item [75], Inventors, delete "Abdul R. Khokhar; Robert A. Newman; Irwin H. Krakoff, all of Houston, Tex." and insert therefor -- Abdul R. Khokhar, of Houston, Tex. --
Item [57], ABSTRACT, in the last paragraph, last line, delete the word "butmay" and substitute therefor -- but may --.

Column 4,
Lines 36 and 37, delete the words "propyliminodiacetato,N-butyliminodiacetato,-Namyliminodiacetato" and substitute therefor -- propyliminodiacetato, N-butyliminodiacetato, N-amyliminodiacetato --.
Line 51, underline "in situ".
Line 58, underline "in vacuo".
Line 67, underline "in situ".

Column 5,
Line 22, underline "in situ".
Line 50, underline "in vacuo".

Column 6,
Lines 22, 35, 40 and 62, underline "in vitro".

Column 7,
Line 9, underline "in vitro".

Signed and Sealed this

Twenty-ninth Day of July, 2003

JAMES E. ROGAN
*Director of the United States Patent and Trademark Office*